United States Patent
Inokuchi et al.

(10) Patent No.: US 9,023,473 B2
(45) Date of Patent: May 5, 2015

(54) SILICONE MICROPARTICLE AND METHOD FOR PRODUCING THE SAME

(75) Inventors: Yoshinori Inokuchi, Annaka (JP); Ryuji Horiguchi, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/564,336

(22) Filed: Aug. 1, 2012

(65) Prior Publication Data

US 2013/0040144 A1 Feb. 14, 2013

(30) Foreign Application Priority Data

Aug. 11, 2011 (JP) ................. 2011-176403

(51) Int. Cl.
| | |
|---|---|
| B32B 27/08 | (2006.01) |
| B05D 7/02 | (2006.01) |
| C08L 83/04 | (2006.01) |
| A61Q 19/00 | (2006.01) |
| A61K 8/02 | (2006.01) |
| C08G 77/04 | (2006.01) |
| C08G 77/12 | (2006.01) |
| C08G 77/20 | (2006.01) |
| C08L 39/00 | (2006.01) |

(52) U.S. Cl.
CPC .............. *C08L 83/04* (2013.01); *C08G 77/045* (2013.01); *C08G 77/12* (2013.01); *C08G 77/20* (2013.01); *C08L 39/00* (2013.01); *C08L 2205/18* (2013.01); *A61Q 19/00* (2013.01); *A61K 8/025* (2013.01); *A61K 2800/10* (2013.01); *A61K 2800/412* (2013.01); *A61K 2800/624* (2013.01); *A61K 2800/654* (2013.01)

(58) Field of Classification Search
None
See application file for complete search history.

(56) References Cited

U.S. PATENT DOCUMENTS

| | | | |
|---|---|---|---|
| 3,159,601 A | 12/1964 | Ashby | |
| 3,159,662 A | 12/1964 | Ashby | |
| 3,220,972 A | 11/1965 | Lamoreaux | |
| 3,775,452 A | 11/1973 | Karstedt | |
| 5,538,793 A | 7/1996 | Inokuchi et al. | |
| 2006/0058440 A1 | 3/2006 | Morita et al. | |
| 2008/0176991 A1* | 7/2008 | Osawa et al. | 524/539 |
| 2010/0112023 A1 | 5/2010 | Inokuchi et al. | |
| 2010/0112074 A1* | 5/2010 | Inokuchi et al. | 424/497 |
| 2010/0203095 A1 | 8/2010 | Inokuchi et al. | |

FOREIGN PATENT DOCUMENTS

| | | |
|---|---|---|
| JP | A-7-196815 | 8/1995 |
| JP | A-2010-132877 | 6/2010 |
| JP | A-2010-132878 | 6/2010 |
| WO | WO 2004/055099 A1 | 7/2004 |

OTHER PUBLICATIONS

Oct. 23, 2012 Extended European Search Report issued in European Patent Application No. 12005630.4.
Packing Land; 2 pages; http://www.packing.co.jp/SIRYOU/gomukoudo1.htm.
Nov. 19, 2013 Office Action issued in Japanese Patent Application No. JP2011-176403 (with partial translation).

* cited by examiner

*Primary Examiner* — Randy Gulakowski
*Assistant Examiner* — Jeffrey Washville
(74) *Attorney, Agent, or Firm* — Oliff PLC

(57) ABSTRACT

The present invention provides a silicone microparticle, wherein the silicone microparticle comprises 100 parts by mass of a silicone elastomer spherical microparticle having volume-average particle diameter of 0.1 to 100 μm and 0.5 to 25 parts by mass of a polyorganosilsesquioxane to cover surface of the silicone elastomer spherical microparticle, wherein the polyorganosilsesquioxane has a shape of granule with the size thereof being 60 nm or less. There can be provided a silicone microparticle having low agglomerating tendency and excellent dispersibility even if rubber hardness of a silicone elastomer microparticle is low and a particle diameter thereof is small.

12 Claims, No Drawings

SILICONE MICROPARTICLE AND METHOD FOR PRODUCING THE SAME

BACKGROUND OF THE INVENTION

1. Field of the Invention

The present invention relates to a silicone microparticle formed of a silicone elastomer spherical microparticle covered with a polyorganosilsesquioxane, and a method for producing the same.

2. Description of the Related Art

With regard to a silicone microparticle, a microparticle having a rubber elasticity (silicone elastomer microparticle) and a microparticle of a polyorganosilsesquioxane resin have been known; and for example, in order to enhance a resistance to cracking of a package caused by stress due to thermal expansion of an electric part, an attempt has been made to blend a silicone elastomer microparticle into a thermosetting resin such as an epoxy resin used for packaging of an electric and an electronic part. However, a silicone elastomer microparticle has high agglomeration tendency and poor dispersibility into a resin so that a stress relaxation effect cannot be obtained fully; and thus, there has been a problem of decreasing a strength of the resin.

To solve the problem as mentioned above, inventors of the present invention proposed a silicone microparticle formed of a silicone elastomer spherical microparticle covered with a polyorganosilsesquioxane (Japanese Patent Laid-Open No. H07-196815); this silicone microparticle has a rubber elasticity and is characterized by low agglomerating tendency and excellent dispersibility into a substrate.

In addition, the silicone microparticle formed of a silicone elastomer spherical microparticle covered with a polyorganosilsesquioxane shown in Japanese Patent Laid-Open No. H07-196815 can be easily broken to primary particles because of low agglomerating tendency; and thus, it can be classified by a dry process with high efficiency. On the other hand, in a silicone elastomer microparticle having high agglomerating tendency, classification thereof is difficult.

In order to provide a cosmetic with a use feeling such as non-stickiness and smoothness and with a spreading property, a silicone microparticle is used. Especially the silicone microparticle formed of a silicone elastomer spherical microparticle covered with a polyorganosilsesquioxane shown in Japanese Patent Laid-Open No. H07-196815 gives a soft feeling, lacks in agglomerating tendency, and has excellent dispersibility; and thus, it is used in many cosmetics.

However, for example, in order to enhance a stress relaxation effect and a soft feeling further, if rubber hardness of the silicone elastomer spherical microparticle portion of the silicone microparticle formed of a silicone elastomer spherical microparticle covered with a polyorganosilsesquioxane shown in Japanese Patent Laid-Open No. H07-196815 is made lower or particle diameter thereof is made smaller, there appears a problem of higher agglomerating tendency and lower dispersibility.

SUMMARY OF THE INVENTION

The present invention was made in view of the situation as mentioned above, and has an object to provide; a silicone microparticle having low agglomerating tendency and excellent dispersibility even if rubber hardness of a silicone elastomer microparticle is low and a particle diameter thereof is small; and a method for producing it.

To solve the problems mentioned above, the present invention provides a silicone microparticle, wherein the silicone microparticle comprises 100 parts by mass of a silicone elastomer spherical microparticle having volume-average particle diameter of 0.1 to 100 µm and 0.5 to 25 parts by mass of a polyorganosilsesquioxane to cover surface of the silicone elastomer spherical microparticle, wherein the polyorganosilsesquioxane has a shape of granule with the size thereof being 60 nm or less.

The silicone microparticle as mentioned above has low agglomerating tendency and excellent dispersibility.

In addition, volume-average particle diameter of the silicone elastomer spherical microparticle may be made 0.1 to 5 µm.

Even if volume-average particle diameter of the silicone elastomer spherical microparticle is made small as described above, the silicone microparticle of the present invention can have low agglomeration tendency.

In addition, rubber hardness of a silicone elastomer to constitute the silicone elastomer spherical microparticle may be 10 or more as measured with a type E durometer and 30 or less as measured with a type A durometer.

Even if rubber hardness of the silicone elastomer to constitute the silicone elastomer spherical microparticle is low as described above, the silicone microparticle of the present invention can have low agglomerating tendency so that it can be dispersed to primary particles even more easily. Because of this, for example, a stress relaxation effect of a resin can be enhanced in the use as a stress relaxation agent of the resin, and a soft feeling can be obtained in the cosmetic use.

In addition, the present invention provides a method for producing a silicone microparticle, wherein a hydrolysis-condensation of an organotrialkoxy silane is carried out in the presence of water, a silicone elastomer spherical microparticle having volume-average particle diameter of 0.1 to 100 µm, an basic substance, and a cationic surfactant and/or a cationic water-soluble polymer, whereby covering surface of the silicone elastomer spherical microparticle with a polyorganosilsesquioxane to produce the silicone microparticle.

According to the method as mentioned above, the silicone microparticle of the present invention can be obtained efficiently by action of a cationic surfactant and a cationic water-soluble polymer.

In addition, it is preferable that amount of the cationic surfactant and/or the cationic water-soluble polymer is 0.001 to 1 part by mass relative to 100 parts by mass of the water.

By using this amount, a covered surface area of the silicone elastomer microparticle with a granular polyorganosilsesquioxane can be made even larger; and thus, the agglomerating tendency can be made further lower.

As mentioned above, the silicone microparticle of the present invention has low agglomeration tendency and excellent dispersibility. Especially, even if rubber hardness of the silicone elastomer microparticle is made lower in order to enhance a stress relaxation effect or particle diameter thereof is made smaller in order to suppress decrease of characteristics such as resin strength or to enhance a stress relaxation effect, there appears no problem of causing higher agglomeration tendency and lower dispersibility. In addition, even if rubber hardness of the silicone elastomer microparticle is made lower in order to obtain a further softer feeling thereby improving a use feeling of a cosmetic, there appears no problem of causing higher agglomeration tendency and lower dispersibility. Accordingly, the silicone microparticle of the present invention is very useful as a stress relaxation agent of a resin and as an enhancer of a use feeling of a cosmetic. In addition, in classification by a dry process, the silicone microparticle of the present invention has low agglomeration tendency so that it can be easily broken to primary particles even if rubber hardness of the silicone elastomer microparticle is low or a particle diameter thereof is small; and thus, high classification performance can be expected.

DESCRIPTION OF THE PREFERRED EMBODIMENTS

Hereinafter, the present invention will be explained in more detail.

As mentioned above, for example, when attempt was made to enhance a stress relaxation effect or to have a further softer feeling, a conventional silicone microparticle formed of a silicone elastomer spherical microparticle covered with a polyorganosilsesquioxane had a problem of causing higher agglomeration tendency and lower dispersibility.

As a result of investigation by the inventors of the present invention, the inventors of the present invention came up with an idea that lower agglomeration tendency and higher dispersibility might be obtained by improving covering property of the polyorganosilsesquioxane. And as a result of further extensive investigation and research by the inventors of the present invention, it was found that the foregoing object could be achieved by the silicone microparticle described below; and based on this finding, the present invention could be accomplished.

Namely, the present invention first provides a silicone microparticle, wherein the silicone microparticle comprises 100 parts by mass of a silicone elastomer spherical microparticle having volume-average particle diameter of 0.1 to 100 μm and 0.5 to 25 parts by mass of a polyorganosilsesquioxane to cover surface of the silicone elastomer spherical microparticle, wherein the polyorganosilsesquioxane has a shape of granule with the size thereof being 60 nm or less.

Here, in the foregoing Japanese Patent Laid-Open No. H07-196815, proposal was made as to a method for performing a hydrolysis-condensation reaction by adding an organotrialkoxy silane and a basic substance or an aqueous basic solution into an aqueous disperse solution of a silicone elastomer microparticle. However, in the microparticle obtained by this method and formed of a silicone elastomer spherical microparticle covered with a polyorganosilsesquioxane, the polyorganosilsesquioxane is adhered in the form of a granule onto surface of the silicone elastomer spherical microparticle, with the size of this granule being about 100 nm. In addition, the inventors of the present invention made a proposal as to a silicone microparticle formed of a silicone elastomer spherical microparticle covered with a polyorganosilsesquioxane in the Japanese Patent Laid-Open No. 2010-132877, Japanese Patent Laid-Open No, 2010-132878, and so on; in these literatures, however, granular size of the polyorganosilsesquioxane to constitute the silicone microparticle to be obtained was about 100 nm.

In view of the above situation, the inventors of the present invention carried out an extensive investigation as to a method for easily producing the silicone microparticle of the present invention as mentioned above. As a result, it was found that if a cationic surfactant or a cationic water-soluble polymer was present in a step of hydrolysis-condensation reaction of an organotrialkoxy silane, diameter of a granular polyorganosilsesquioxane to cover surface of a silicone elastomer spherical microparticle could be made small.

The present invention secondly provides a method for producing a silicone microparticle, wherein a hydrolysis-condensation of an organotrialkoxy silane is carried out in the presence of water, a silicone elastomer spherical microparticle having volume-average particle diameter of 0.1 to 100 μm, an basic substance, and a cationic surfactant and/or a cationic water-soluble polymer, whereby covering surface of the silicone elastomer spherical microparticle with a polyorganosilsesquioxane to produce the silicone microparticle.

Hereinafter, the present invention will be explained in more detail.

<Silicone Microparticle>

The silicone microparticle of the present invention is formed of a silicone elastomer spherical microparticle and a granular polyorganosilsesquioxane to cover surface of the silicone elastomer spherical microparticle with size of the granule being 60 nm or less, wherein amount of the polyorganosilsesquioxane is 0.5 to 25 parts by mass, or preferably 1 to 15 parts by mass, relative to 100 parts by mass of the silicone elastomer spherical microparticle. If amount of the polyorganosilsesquioxane is less than 0.5 part by mass, it will lead to higher agglomeration tendency and poor dispersibility; and if the amount is more than 25 parts by mass, it will deteriorate a stress relaxation effect and a soft feeling.

Silicone Elastomer Spherical Microparticle

In the silicone microparticle of the present invention, volume-average particle diameter of the silicone elastomer spherical microparticle whose surface is covered with the polyorganosilsesquioxane is 0.1 to 100 μm, or preferably 0.1 to 40 μm. If volume-average particle diameter of the silicone elastomer spherical microparticle is less than 0.1 μm, the silicone microparticle to be obtained therefrom has higher agglomeration tendency; and thus, dispersion till primary particles is not easy. On the other hand, if volume-average particle diameter of the silicone elastomer spherical microparticle is larger than 100 μm, not only characteristics such as strength of a substrate resin are deteriorated but also a stress relaxation effect is not fully expressed in the use area as a stress relaxation agent of a resin, while non-stickiness and smoothness are deteriorated and a rough feeling is felt in the cosmetic use area. The present invention has a characteristic that low agglomeration tendency can be obtained even if volume-average particle diameter of the silicone elastomer spherical microparticle is small, though more preferable diameter thereof is 5 μm or less.

Meanwhile, the volume-average particle diameter can be measured by selecting an appropriate method from any of a microscopic method, a light-scattering method, a laser diffraction method, a liquid sedimentation method, an electric resistance method, and so on, in accordance with particle diameter. In this specification, the term "spherical" means that shape of the microparticle is not only a perfectly spherical shape but also a deformed ball with the average ratio of length of the longest axis to length of the shortest axis (aspect ratio) being usually in the range of 1 to 4, preferably 1 to 2, more preferably 1 to 1.6, or still more preferably 1 to 1.4. Shape of the microparticle can be confirmed by observation of the microparticle with an optical microscope or an electron microscope.

The silicone elastomer to constitute the silicone elastomer spherical microparticle is preferably not sticky and rubber hardness thereof in its soft side is preferably 10 or more as measured by the E-type durometer in accordance with JIS K 6253, and 90 or less in its hard side as measured by the A-type durometer. More preferable hardness is 20 or more by the E-type durometer and 80 or less by the A-type durometer. If the hardness is less than 10 by the E-type durometer, the obtained silicone microparticle has higher agglomeration tendency so that dispersion thereof till primary particles may be difficult. If the hardness thereof is more than 90 by the A-type durometer, there is a fear of decrease in a stress relaxation effect of a resin in the use area as a stress relaxation agent of a resin, while there is a fear of deterioration in a soft feeling in the cosmetic use area. The present invention has a characteristic of low agglomeration tendency even if rubber hardness is low; and thus, still more preferable hardness is 30 or less by the A-type durometer.

The silicone elastomer is a cured product having a linear organosiloxane block shown by, for example, the formula of —($R^1_2SiO_{2/2}$)$_n$—. In this formula, $R^1$ represents a substituted or an unsubstituted monovalent hydrocarbon group having 1 to 30 carbon atoms, and "n" represents a positive number ranging from 5 to 5000.

Illustrative examples of $R^1$ include an alkyl group such as a methyl group, an ethyl group, a propyl group, a butyl group, a pentyl group, a hexyl group, a heptyl group, an octyl group, a decyl group, an undecyl group, a dodecyl group, a tetradecyl group, a pentadecyl group, a hexadecyl group, a heptadecyl group, an octadecyl group, a nonadecyl group, an eicosyl group, a henicosyl group, a docosyl group, a tricosyl group, a tetracyl group, and a triacotyl group; an aryl group such as a phenyl group, a tolyl group, and a naphthyl group; an aralkyl group such as a benzyl group and a phenethyl group; an alkenyl group such as a vinyl group and an allyl group; a cycloalkyl group such as a cyclopentyl group, a cyclohexyl group, and a cycloheptyl group; and a hydrocarbon group whose part or all of hydrogen atoms bonded to a carbon atom of these groups is substituted with an atom such as a halogen atom (fluorine atom, chlorine atom, bromine atom, and iodine atom) and/or a substituent group, while illustrative examples of the said substituent group include an acryloyloxy group, a methacryloyloxy group, an epoxy group, a glycidoxy group, and a carboxyl group.

The silicone elastomer is obtained from a curable liquid silicone composition.

Illustrative examples of the curing reaction thereof include a condensation reaction between a methoxy silyl group (≡SiOCH$_3$) and a hydroxy silyl group (≡SiOH), and so on; a radical reaction between a mercaptopropyl silyl group (≡Si—C$_3$H$_6$SH) and a vinyl silyl group (≡SiCH═CH$_2$); and an addition reaction between a vinyl silyl group (≡SiCH═CH$_2$) and a hydrosilyl group (≡SiH); however, in view of reactivity, an addition reaction is preferable.

For example, if the silicone elastomer is obtained by curing with an addition reaction, in any one of a combination of an organopolysiloxane shown by the average formula of $R^2_aR^3_bSiO_{(4-a-b)/2}$ having at least 2 monovalent olefinic unsaturated groups in a molecule with an organohydrogen polysiloxane shown by the average formula of $R^4_cH_dSiO_{(4-c-d)/2}$ having at least 3 silicon-bonded hydrogen atoms in a molecule and a combination of an organopolysiloxane shown by the average formula of $R^2_aR^3_bSiO_{(4-a-b)/2}$ having at least 3 monovalent olefinic unsaturated groups in a molecule with an organohydrogen polysiloxane shown by the average formula of $R^4_cH_dSiO_{(4-c-d)/2}$ having at least 2 silicon-bonded hydrogen atoms in a molecule, the addition reaction of the liquid silicone composition may be carried out in the presence of a platinum group metal-based catalyst with the blending ratio of the hydrosilyl group to the monovalent olefinic unsaturated group, contained in the organopolysiloxane having monovalent olefinic unsaturated groups and the organohydrogen polysiloxane, being 0.5 to 2.

Here, $R^2$ in the above formula represents a substituted or an unsubstituted monovalent hydrocarbon group having 1 to 30 carbon atoms except for aliphatic unsaturated group, and $R^3$ represents monovalent olefinic unsaturated group having 2 to 6 carbon atoms. "a" and "b" represent positive numbers satisfying that $0<a<3$, $0<b\leq3$, and $0.1\leq a+b\leq3$, or preferably $0<a\leq2.295$, $0.005\leq b\leq2.3$, and $0.5\leq a+b\leq2.3$. $R^4$ represents a substituted or an unsubstituted monovalent hydrocarbon group having 1 to 30 carbon atoms except for aliphatic unsaturated group. "c" and "d" represent positive numbers satisfying that $0<c<3$, $0<d\leq3$, and $0.1\leq c+d\leq3$, or preferably $0<c\leq2.295$, $0.005\leq c\leq12.3$, and $0.5\leq c+d\leq2.3$.

Illustrative examples of $R^2$ include an alkyl group such as a methyl group, an ethyl group, a propyl group, a butyl group, a pentyl group, a hexyl group, a heptyl group, an octyl group, a decyl group, an undecyl group, a dodecyl group, a tetradecyl group, a pentadecyl group, a hexadecyl group, a heptadecyl group, an octadecyl group, a nonadecyl group, an eicosyl group, a henicosyl group, a docosyl group, a tricosyl group, a tetracyl group, and a triacotyl group; an aryl group such as a phenyl group, a tolyl group, and a naphthyl group; an aralkyl group such as a benzyl group and a phenethyl group; a cycloalkyl group such as a cyclopentyl group, a cyclohexyl group, and a cycloheptyl group; and a hydrocarbon group whose part or all of hydrogen atoms bonded to a carbon atom of these groups is substituted with an atom such as a halogen atom (fluorine atom, chlorine atom, bromine atom, and iodine atom) and/or a substituent group, while illustrative examples of the said substituent group include an acryloyloxy group, a methacryloyloxy group, an epoxy group, a glycidoxy group, and a carboxyl group. However, 50% or more by mole of all the $R^2$ are preferable industrially.

Illustrative examples of $R^3$ include a vinyl group, an allyl group, a propenyl group, a butenyl group, a pentenyl group, and a hexenyl group, but a vinyl group is preferable industrially. Illustrative examples of $R^4$ include the same groups as those exemplified above for $R^2$.

Dynamic viscosities at 25° C. of the organopolysiloxane having olefinic unsaturated groups and the organohydrogen polysiloxane are preferably 100,000 mm$^2$/second or less, or more preferably 10,000 mm$^2$/second or less, because if the dynamic viscosity of them is higher than 100,000 mm$^2$/second, the particle having a narrow molecular weight range is difficult to be obtained in the production process described later. The organopolysiloxane having olefinic unsaturated groups and the organohydrogen polysiloxane may be of any of a linear, a cyclic, and a branched structure, but a linear structure is especially preferable. Meanwhile, these dynamic viscosities are the values measured by an Ostwald viscometer.

As mentioned above, the combination of an organopolysiloxane having at least 2 monovalent olefinic unsaturated groups in a molecule with an organohydrogen polysiloxane having at least 3 silicon-bonded hydrogen atoms in a molecule or the combination of an organopolysiloxane having at least 3 monovalent olefinic unsaturated groups in a molecule with an organohydrogen polysiloxane having at least 2 silicon-bonded hydrogen atoms in a molecule is necessary. Unless structures and combination of the polysiloxanes are made as mentioned above, a sticky cured elastomer may be obtained.

As to the platinum group metal-based catalyst, a heretofore known catalyst used in a hydrosilylation reaction may be used. Specific examples thereof include a single body of a metal belonging to the platinum group such as platinum (including platinum black), rhodium, and palladium; a platinum chloride, a chloroplatinic acid, and a chloroplatinate, such as H$_2$PtCl$_4$.kH$_2$O, H$_2$PtCl$_6$.kH$_2$O, NaHPtCl$_6$.kH$_2$O, KHPtCl$_6$.kH$_2$O, Na$_2$PtCl$_6$.kH$_2$O, K$_2$PtCl$_4$.kH$_2$O, PtCl$_4$.kH$_2$O, PtCl$_2$, and Na$_2$HPtCl$_4$.kH$_2$O, wherein "k" represents an integer of 0 to 6, or preferably 0 or 6; an alcohol-modified chloroplatinic acid (see, U.S. Pat. No. 3,220,972); a complex of chloroplatinic acid with an olefin (see, U.S. Pat. No. 3,159,601, U.S. Pat. No. 3,159,662, and U.S. Pat. No. 3,775,452); a metal belonging to the platinum group, such as platinum black and palladium, with these metals being supported on a carrier such as alumina, silica, and carbon; a rhodium-olefin complex; chlorotris(triphenylphosphine) rhodium (Wilkinson catalyst); and a complex of platinum chloride, chloroplatinic acid, or chloroplatinate with a vinyl-containing siloxane, in particular a vinyl-containing cyclic siloxane.

As to adding amount of the platinum group metal-based catalyst, an effective amount for a hydrosilylation reaction may be used. The amount of the metal belonging to the platinum group in the catalyst is usually about 0.1 to about 500 ppm by mass, preferably about 0.5 to about 200 ppm by mass, or more preferably about 1 to about 100 ppm by mass, relative to entirety of the curable liquid silicone composition.

The silicone elastomer spherical microparticle to constitute the silicone microparticle of the present invention may contain a silicone oil, an organosilane, an inorganic powder, an organic powder, and so on in its particle.

The silicone elastomer microparticle may be produced as a form of an aqueous disperse solution by a heretofore known method. For example, in the case of producing the silicone elastomer by curing with an addition reaction, the addition reaction may be carried out by adding a platinum group metal-based catalyst to an emulsion obtained by emulsifying a liquid silicone composition comprising the organopolysiloxane having olefinic unsaturated groups and the organohydrogen polysiloxane, the composition thereof being added with a surfactant and water.

The surfactant used herein is a nonionic surfactant, a cationic surfactant, or an amphoteric surfactant. An anionic surfactant may suppress an action of a cationic surfactant or a cationic water-soluble polymer used in a step of covering with a polyorganosilsesquioxane as described later, or may impair dispersibility of the silicone elastomer spherical microparticle at the time of adding a cationic surfactant or a cationic water-soluble polymer whereby causing agglomeration in a certain case.

Illustrative examples of the nonionic surfactant include a polyoxyethylene alkyl ether, a polyoxyethylene polyoxypropylene alkyl ether, a polyoxyethylene alkyl phenyl ether, a polyethylene glycol fatty acid ester, a sorbitan fatty acid ester, a polyoxyethylene sorbitan fatty acid ester, a polyoxyethylene sorbit fatty acid ester, a glycerin fatty acid ester, a polyoxyethylene glycerin fatty acid ester, a polyglycerin fatty acid ester, a propylene glycol fatty acid ester, a polyoxyethylene castor oil, a polyoxyethylene cured castor oil, a polyoxyethylene cured castor oil fatty acid ester, a polyoxyethylene alkyl amine, a polyoxyethylene fatty acid amid, an organopolysiloxane modified with polyoxyethylene, and an organopolysiloxane modified with polyoxyethylene polyoxypropylene.

Illustrative examples of the cationic surfactant include an alkyl trimethyl ammonium salt, a dialkyl dimethyl ammonium salt, a polyoxyethylene alkyl dimethyl ammonium salt, a dipolyoxyethylene alkyl methyl ammonium salt, a tripolyoxyethylene alkyl ammonium salt, an alkyl benzyl dimethyl ammonium salt, an alkyl pyridinium salt, a monoalkyl amine salt, and a monoalkylamide amine salt.

Illustrative examples of the amphoteric surfactant include an alkyl dimethyl amine oxide, an alkyl dimethyl carboxybetaine, an alkylamide propyl dimethyl carboxybetaine, an alkyl hydroxysulfobetaine, and an alkyl carboxymethyl hydroxyethyl imidazolinium betaine.

These surfactants may be used singly or as a mixture of two or more of them, while a nonionic surfactant is preferable because it can emulsify the liquid silicone composition with a small amount and can give a fine particle. If use amount of the surfactant is too large, covering with a polyorganosilsesquioxane in the production process described later becomes difficult. Use amount the surfactant is preferably 20 or less by mass relative to 100 parts by mass of the liquid silicone composition. If the amount thereof is less than 0.01 part by mass, it is difficult to obtain a fine particle in a certain case; and thus, the amount is preferably in the range of 0.01 to 20 parts by mass, or more preferably 0.05 to 5 parts by mass.

For emulsification, a general emulsification equipment for dispersion may be used; and illustrative examples thereof include a centrifugal throwing-out type agitator of high-speed rotation such as a homodisper; a shearing type agitator of high-speed rotation such as a homomixer; a high-pressure, injection-type emulsification disperser such as a homogenizer; a colloid mill; and an ultrasonic emulsifier.

If dispersibility of a platinum group metal-based catalyst into water is poor, it is preferable that the catalyst be added into an emulsion in the state of being dissolved in a surfactant. Surfactants mentioned above may be used, while a nonionic surfactant is especially preferable.

The addition reaction may be carried out at room temperature; but if the reaction is incomplete, the reaction may be carried out with heating at the temperature of less than 100° C.

Polyorganosilsesquioxane

In the silicone microparticle of the present invention, the polyorganosilsesquioxane to cover surface of the silicone elastomer spherical microparticle has a shape of granule; and the diameter thereof is 60 nm or less, or preferably 40 nm or less. If a granule of the polyorganosilsesquioxane is larger than 60 nm, there is a tendency of higher agglomeration and lower dispersibility. If the smaller a granule of the polyorganosilsesquioxane is, the larger an area thereof to cover surface of the silicone elastomer microparticle becomes, or in other words, the larger the area rate of the polyorganosilsesquioxane to cover surface of the silicone elastomer microparticle becomes, whereby assumingly decreases the agglomeration tendency. Diameter of the polyorganosilsesquioxane may be confirmed by observation of the particle with an electron microscope.

Meanwhile, smaller size (diameter) of the polyorganosilsesquioxane granule is better; and a lower limit value thereof is not particularly specified.

The polyorganosilsesquioxane is a resinous solid whose unit shown by the formula of $R^5SiO_{3/2}$ is crosslinked in the three-dimensional reticulate form. In the present invention, $R^5$ in the formula represents a substituted or an unsubstituted monovalent hydrocarbon group having 1 to 20 carbon atoms. Illustrative examples of $R^5$ include an alkyl group such as a methyl group, an ethyl group, a propyl group, a butyl group, a pentyl group, a hexyl group, a heptyl group, an octyl group, a decyl group, a undecyl group, a dodecyl group, a tetradecyl group, a pentadecyl group, a hexadecyl group, a heptadecyl group, an octadecyl group, a nonadecyl group, and an eicosyl group; an alkenyl group such as a vinyl group and an allyl group; an aryl group such as a phenyl group, a tolyl group, and a naphthyl group; an aralkyl group such as a benzyl group and a phenethyl group; a cycloalkyl group such as a cyclopentyl group, a cyclohexyl group, and a cycloheptyl group; and a hydrocarbon group whose part or all of hydrogen atoms bonded to a carbon atom of these groups is substituted with an atom such as a halogen atom (fluorine atom, chlorine atom, bromine atom, and iodine atom) and/or a substituent group, while illustrative example of the substituent group includes an amino group, an acryloyloxy group, a methacryloyloxy group, an epoxy group, a glycidoxy group, a mercapto group, and a carboxyl group. To cover with the polyorganosilsesquioxane by the method described later, this $R^5$ is preferably a methyl group, a vinyl group, or a phenyl group with the amount thereof being 50% or more by mole, more preferably 80% or more by mole, or still more preferably 90% or more by mole.

The polyorganosilsesquioxane may contain, in addition to the unit shown by $R^5SiO_{3/2}$, at least one of the units shown by $R^5{}_2SiO_{2/2}$, $R^5{}_3SiO_{1/2}$, and $SiO_{4/2}$. In the polyorganosilsesquioxane like this, amount of the unit shown by $R^5SiO_{3/2}$ is preferably 70 to 100% by mole, or more preferably 80 to 100% by mole, relative to entirety of the siloxane units.

<Preparation Method>

The silicone microparticle of the present invention can be obtained by hydrolysis-condensation of an organotrialkoxy silane in the presence of water, a silicone elastomer spherical microparticle having volume-average particle diameter of 0.1 to 100 μm, a basic substance, and a cationic surfactant and/or a cationic water-soluble polymer, whereby covering surface of the silicone elastomer spherical microparticle with a polyorganosilsesquioxane.

Silicone Elastomer Spherical Microparticle

A silicone elastomer spherical microparticle having the volume-average particle diameter of 0.1 to 100 μm and produced, for example, in the form of the above-mentioned aqueous disperse solution as it stands or additionally added with water, may be used. Amount of the silicone elastomer spherical microparticle is preferably 1 to 150 parts by mass, or more preferably 5 to 70 parts by mass, relative to 100 parts by mass of water. If the amount is less than 1 part by mass, there is a fear of lower production efficiency of the intended silicone microparticle; while if the amount is more than 150 parts by mass, covering of surface of the silicone elastomer spherical microparticle with a polyorganosilsesquioxane resin becomes difficult so that agglomeration or melt adhesion of the particles may occur in a certain case.

Cationic Surfactant and Cationic Water-Soluble Polymer

A cationic surfactant and a cationic water-soluble polymer have an effect to make diameter of a granular polyorganosilsesquioxane to cover surface of the silicone elastomer spherical microparticle smaller.

A cationic surfactant and a cationic water-soluble polymer may be used singly or as a mixture of two or more of them, while a cationic water-soluble polymer is more preferable because an odor is easily generated during a thermal drying process in a later step if a cationic surfactant remains in the silicone microparticles.

Adding amount of the cationic surfactant and/or the cationic water-soluble polymer is preferably 0.001 to 1 part by mass, or more preferably 0.005 to 0.5 part by mass, relative to 100 parts by mass of water. If the amount is less than 0.001 part by mass, it becomes difficult to make diameter of the polyorganosilsesquioxane smaller; on the other hand, if the amount is more than 1 part by mass, it becomes difficult to cover surface of the silicone elastomer spherical microparticle with the polyorganosilsesquioxane.

The cationic surfactant is not particularly restricted, and illustrative examples thereof include those mentioned above.

The cationic water-soluble polymer is not particularly restricted either. Illustrative examples thereof include a polymer of dimethyl diallyl ammonium chloride; a polymer of vinyl imidazoline; a polymer of methyl vinyl imidazolium chloride; a polymer of acrylic acid ethyl trimethyl ammonium chloride; a polymer of methacrylic acid ethyl trimethyl ammonium chloride; a polymer of acrylamide propyl trimethyl ammonium chloride; a polymer of methacrylamide propyl trimethyl ammonium chloride; a polymer of epichlorohydrin and dimethylamine; a polymer of ethylene imine; a quaternary compound of polyethylene imine; a polymer of allylamine hydrochloride salt; polylysine; a cationic starch; a cationic cellulose; chitosan; and a derivative of these substances copolymerized or the like with a monomer containing a nonionic group and an anionic group.

Basic Substance

A basic substance serves as a catalyst for a hydrolysis-condensation reaction of an organotrialkoxy silane. The basic substance may be used singly, or as a mixture of two or more of them. The basic substance may be added as it is or as a basic aqueous solution. It is preferable that the basic substance is added before an organotrialkoxy silane is added into an aqueous disperse solution containing water, a silicone elastomer spherical microparticle, and a cationic surfactant or a cationic water-soluble polymer. If the basic substance is added after addition of an organotrialkoxy silane, there is a certain case that surface of a silicone elastomer spherical microparticle is not covered with a polyorganosilsesquioxane.

Adding amount of the basic substance is such that pH of an aqueous disperse solution, containing water, a silicone elastomer spherical microparticle, a cationic surfactant and/or a cationic water-soluble polymer, and the basic substance, may become preferably in the range of 10.0 to 13.0, or more preferably 10.5 to 12.5. If the basic substance is added with the amount such that the pH may become in the range of 10.0 to 13.0, the hydrolysis-condensation reaction of an organotrialkoxy silane and covering of surface of a silicone elastomer spherical microparticle with a polyorganosilsesquioxane may take place especially well.

The basic substance is not particularly restricted. Illustrative examples thereof include an alkaline metal hydroxide such as potassium hydroxide, sodium hydroxide, and lithium hydroxide; an alkaline earth metal hydroxide such as calcium hydroxide and barium hydroxide; an alkali metal carbonate such as potassium carbonate and sodium carbonate; ammonia; a tetraalkyl ammonium hydroxide such as tetramethyl ammonium hydroxide and tetraethyl ammonium hydroxide; and an amine such as monomethyl amine, monoethyl amine, monopropyl amine, monobutyl amine, monopentyl amine, dimethyl amine, diethyl amine, trimethyl amine, triethanol amine, and ethylene diamine. Among them, ammonia is most preferable because it can be easily removed from obtained silicone microparticle powders by evaporation. Ammonia of a commercially available aqueous ammonium solution may be used.

Organotrialkoxy Silane

An organotrialkoxy silane shown, for example, by the formula of $R^5Si(OR^6)_3$ may be used. In this formula, $R^5$ represents the same meanings as before and $R^6$ represents an unsubstituted monovalent hydrocarbon group having 1 to 6 carbon atoms. Illustrative examples of $R^6$ include a methyl group, an ethyl group, a propyl group, a butyl group, a pentyl group, and a hexyl group, while a methyl group is preferable in view of its reactivity. In the case of intending to further introduce at least one unit of the units shown by $R^5{}_2SiO_{2/2}$, $R^5{}_3SiO_{1/2}$, and $SiO_{4/2}$ into a polyorganosilsesquioxane, at least one compound, corresponding to the respective units, shown by $R^5{}_2Si(OR^6)_2$, $R^5{}_3SiOR^6$, or $Si(OR^6)_4$, may be added (in these formulae, $R^5$ and $R^6$ represent the same meanings as before). In the case of using the compound shown by $R^5Si(OR^6)_3$ and at least one of the compounds shown by $R^5{}_2Si(OR^6)_2$, $R^5{}_3SiOR^6$, and $Si(OR^6)_4$ as raw materials for the polyorganosilsesquioxane, the content of $R^5Si(OR^6)_3$ therein is preferably 70 to 100% by mole, or more preferably 80 to 100% by mole, relative to totality of the raw materials.

Adding amount of the organotrialkoxy silane is such that content of the polyorganosilsesquioxane may become in the range of 0.5 to 25 parts by mass, or preferably 1 to 15 parts by mass, relative to 100 parts by mass of the silicone elastomer spherical microparticle.

Addition of the organotrialkoxy silane is done preferably under agitation by using a usual agitator having a propeller blade, a plate blade, and so on. The organotrialkoxy silane may be added all at once, but gradual addition over time is preferable. Temperature during this operation is preferably in the range of 0 to 60° C., or more preferably 0 to 40° C. If the temperature is in the range of 0 to 60° C., surface of the silicone elastomer spherical microparticle can be covered well with the polyorganosilsesquioxane.

After addition of the organotrialkoxy silane, agitation is continued until the hydrolysis-condensation reaction of the organotrialkoxy silane is completed. To complete the hydrolysis-condensation reaction, the reaction may be carried out at room temperature or with heating at about 40 to about 100° C.

After the hydrolysis-condensation reaction, water is removed from the obtained aqueous disperse solution of the silicone microparticle of the present invention. Water may be removed, for example, by heating the aqueous disperse solution after the reaction under normal pressure or reduced pressure; specific examples of the method thereof include a method to remove water by heating the disperse solution under a static condition, a method to remove water by heating the disperse solution under fluidized condition by agitation, a method to spray and disperse the disperse solution into a hot air stream such as a spray dryer, and a method using a fluid heating medium. Meanwhile, as the pre-treatment of this operation, the disperse solution may be concentrated by thermal dehydration, separation by filtration, centrifugal separation, decantation, and so on; the disperse solution may be rinsed with water or an alcohol, if necessary.

If the product obtained by removing water from the aqueous disperse solution after reaction is agglomerated, the product may be crushed by a crushing equipment such as a jet mill, a ball mill, and a hammer mill to obtain the silicone microparticle.

EXAMPLES

Hereinafter, the present invention will be explained in more detail by showing Examples and Comparative Examples; but the present invention is not limited to these Examples. Meanwhile, in these Examples, a dynamic viscosity is the value measured at 25° C., and "%" used to show concentration and content means "% by mass", Evaluation of dispersibility was done as following.

<Evaluation of Dispersibility (Measurement of Sieve-Passed Amount)>

A sieve of 60 mesh, a sieve of 100 mesh, and a sieve of 200 mesh were stacked from top to bottom in order; and a weighed microparticle sample of about 2 g was put on the sieve of 60 mesh. Then, it was vibrated with the vibration amplitude of 1 mm for 90 seconds by using Powder Tester PT-E Type (powder characterization equipment manufactured by Hosokawa Micron Corp.) to measure respective amounts passed through each sieve. Sieve-passed amount was shown by "%", and it was judged that larger the passed amount, higher the dispersibility.

Example 1

Into a 1-L glass beaker were taken 500 g of a methyl vinyl polysiloxane having a dynamic viscosity of 600 mm²/second as shown by the following formula (1) and 20 g of a methyl hydrogen polysiloxane having a dynamic viscosity of 30 mm²/second as shown by the following formula (2) (blending ratio of the hydrosilyl group to the olefinic unsaturated group is 0.90 to 1), and they were dissolved by agitation with a homomixer at 2000 rpm. Thereafter, 5 g of polyoxyethylene octyl phenyl ether (addition number of moles of ethylene oxide is 9 mole) and 150 g of water were added thereinto; and then, the resulting mixture was agitated by using a homomixer at 6000 rpm, whereby giving an oil-in-water state having increased viscosity; the agitation was continued for further 15 minutes. Then, 329 g of water was added thereinto with agitation at 2000 rpm to obtain a white, homogenous emulsion. This emulsion was transferred to a 1-L glass flask equipped with an agitator having an anchor blade; and after the temperature thereof was adjusted at 15 to 20° C., a dissolved mixture solution comprising 1 g of a toluene solution of a chloroplatinic acid-olefin complex (Pt content of 0.5%) and 1 g of polyoxyethylene octyl phenyl ether (addition number of moles of ethylene oxide is 9 mole) was added thereinto under agitation; and then, the resulting mixture was agitated for 12 hours at the same temperature to obtain an aqueous disperse solution of silicone elastomer microparticles.

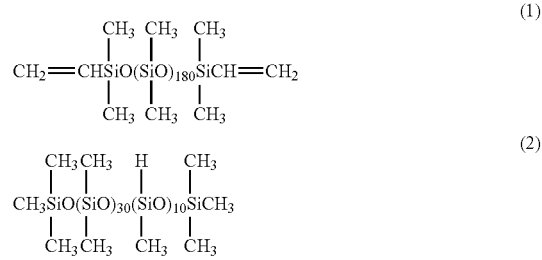

Shape of the silicone elastomer microparticle in the aqueous disperse solution thus obtained was spherical by observation with an optical microscope; and the volume-average particle diameter thereof measured by a particle size distribution measurement instrument using an electric resistance method (Multisizer 3; manufactured by Beckman Coulter, Inc.) was 3 µm.

Hardness of the silicone elastomer to constitute the silicone elastomer microparticle was measured as following. A methyl vinyl polysiloxane shown by the formula (1), a methyl hydrogen polysiloxane shown by the formula (2), and a toluene solution of a chloroplatinic acid-olefin complex (Pt content of 0.5%) were mixed with the foregoing mixing ratio; and then, the resulting mixture was poured into an aluminum petri dish so as to give the depth of 10 mm. It was allowed to stand at 25° C. for 24 hours, and then heated in a constant temperature oven controlled at 50° C. for one hour to obtain an unsticky silicone elastomer. Hardness of the silicone elastomer was 25 as measured with a durometer A hardness meter.

Into a 3-L glass flask equipped with an agitator having an anchor blade was transferred 580 g of the aqueous disperse solution containing the silicone elastomer spherical particles obtained as described above; and thereinto were added 2290 g of water, 60 g of a 28% aqueous ammonia solution, and 3.3 g (this amount corresponds to 0.05 part by mass of dimethyl diallyl ammonium chloride polymer relative to 100 parts by mass of water) of a 40% aqueous solution of dimethyl diallyl ammonium chloride polymer (trade name of ME Polymer H40W; manufactured by Toho Chemical Industry Co., Ltd.). At this point of time, pH of the solution was 11.3. After the temperature of the resulting mixture was adjusted at 5 to 10° C., 65 g of methyl trimethoxy silane (this amount corresponds to 10.7 parts by mass of the polymethylsilsesquioxane after the hydrolysis-condensation reaction relative to 100 parts by mass of the silicone elastomer spherical microparticle) was gradually added thereinto over 20 minutes; and then, agitation was further continued for one hour while maintaining the solution temperature at 5 to 10° C. Then, the temperature thereof was raised till 55 to 60° C.; and then, agitation was continued for one hour while maintaining the same temperature to complete the hydrolysis-condensation reaction of methyl trimethoxy silane.

The solution obtained after the hydrolysis-condensation reaction of methyl trimethoxy silane in the aqueous disperse solution of the silicone elastomer microparticles was dehydrated by using a filter press till water content therein of about 30%. The dehydrated matter was transferred to a 5-L glass flask equipped with an agitator having an anchor blade, and then, 3000 g of water was added thereinto; after agitation was continued for 30 minutes, dehydration was done by using a filter press. The dehydrated matter thus obtained was transferred again to the 5-L glass flask equipped with an agitator having an anchor blade, added with 3000 g of water, agitated for 30 minutes, and then dehydrated by using a filter press. The dehydrated matter was dried with a fluidized bed drier using a hot air of 105° C.; then, the dried matter thus obtained was crushed with a jet mill to obtain free-flowing silicone microparticles.

The silicone microparticles thus obtained were dispersed into water by using a surfactant; and particle size distribution similar to that of the aqueous disperse solution of the foregoing silicone elastomer microparticles, having volume-average particle diameter of 3 µm, was obtained by a particle size distribution measurement instrument using an electric resistance method (Multisizer 3; manufactured by Beckman Coulter, Inc.).

It was confirmed by observation with an electron microscope that this silicone microparticle was a microparticle whose silicone elastomer spherical microparticle surface was covered with a granular polymethylsilsesquioxane having diameter of 10 to 20 nm.

Dispersibility of this silicone microparticle was measured by the method described before; and the results shown in Table 1 were obtained.

Example 2

A silicone microparticle was obtained in a manner similar to that in Example 1 except that 1.3 g (this amount corresponds to 0.05 part by mass relative to 100 parts by mass of water) of a cationic cellulose (trade name of Poise C-60H; manufactured by Kao Corp.) was used instead of 3.3 g of the 40% aqueous solution of dimethyl diallyl ammonium chloride polymer (trade name of ME Polymer H40W; manufactured by Toho Chemical Industry Co., Ltd.) in Example 1.

The silicone microparticles thus obtained were dispersed into water by using a surfactant; and particle size distribution similar to that of the aqueous disperse solution of the foregoing silicone elastomer microparticles, having volume-average particle diameter of 3 µm, was obtained by a particle size distribution measurement instrument using an electric resistance method (Multisizer 3; manufactured by Beckman Coulter, Inc.).

It was confirmed by observation with an electron microscope that this silicone microparticle was a microparticle whose silicone elastomer spherical microparticle surface was covered with a granular polymethylsilsesquioxane having diameter of 30 to 60 nm.

Dispersibility of this silicone microparticle was measured by the method described before; and the results shown in Table 1 were obtained.

Example 3

A silicone microparticle was obtained in a manner similar to that in Example 1 except that 4.4 g (this amount corresponds to 0.05 part by mass of dodecyl trimethyl ammonium chloride relative to 100 parts by mass of water) of 30% dodecyl trimethyl ammonium chloride (trade name of Cation BB; manufactured by NOF Corp.) was used instead of 3.3 g of the 40% aqueous solution of dimethyl diallyl ammonium chloride polymer (trade name of ME Polymer H40W; manufactured by Toho Chemical Industry Co., Ltd.) in Example 1.

The silicone microparticles thus obtained were dispersed into water by using a surfactant; and particle size distribution similar to that of the aqueous disperse solution of the foregoing silicone elastomer microparticles, having volume-average particle diameter of 3 µm, was obtained by a particle size distribution measurement instrument using an electric resistance method (Multisizer 3; manufactured by Beckman Coulter, Inc.).

It was confirmed by observation with an electron microscope that this silicone microparticle was a microparticle whose silicone elastomer spherical microparticle surface was covered with a granular polymethylsilsesquioxane having diameter of 20 to 30 nm.

Dispersibility of this silicone microparticle was measured by the method described before; and the results shown in Table 1 were obtained.

Example 4

A silicone microparticle was obtained in a manner similar to that in Example 1 except that 4.4 g (this amount corresponds to 0.05 part by mass of polyethylene imine relative to 100 parts by mass of water) of 30% polyethylene imine (trade name of Epomine P-1000; manufactured by Nippon Shokubai Co., Ltd.) was used instead of 3.3 g of the 40% aqueous solution of dimethyl diallyl ammonium chloride polymer (trade name of ME Polymer H40W; manufactured by Toho Chemical Industry Co., Ltd.) in Example 1.

The silicone microparticles thus obtained were dispersed into water by using a surfactant; and particle size distribution similar to that of the aqueous disperse solution of the foregoing silicone elastomer microparticles, having volume-average particle diameter of 3 µm, was obtained by a particle size distribution measurement instrument using an electric resistance method (Multisizer 3; manufactured by Beckman Coulter, Inc.).

It was confirmed by observation with an electron microscope that this silicone microparticle was a microparticle whose silicone elastomer spherical microparticle surface was covered with a granular polymethylsilsesquioxane having diameter of 30 to 40 nm.

Dispersibility of this silicone microparticle was measured by the method described before; and the results shown in Table 1 were obtained.

Example 5

A silicone microparticle was obtained in a manner similar to that in Example 1 except that 1.8 g (this amount corresponds to 0.05 part by mass of dialkyl (carbon number of 12 to 18) dimethyl ammonium chloride relative to 100 parts by mass of water) of 75% dialkyl (carbon number of 12 to 18) dimethyl ammonium chloride (trade name of Coatamine D2345P; manufactured by Kao Corp.) was used instead of 3.3 g of the 40% aqueous solution of dimethyl diallyl ammonium chloride polymer (trade name of ME Polymer H40W; manufactured by Toho Chemical Industry Co., Ltd.) in Example 1.

The silicone microparticles thus obtained were dispersed into water by using a surfactant; and particle size distribution similar to that of the aqueous disperse solution of the foregoing silicone elastomer microparticles, having volume-average particle diameter of 3 µm, was obtained by a particle size distribution measurement instrument using an electric resistance method (Multisizer 3; manufactured by Beckman Coulter, Inc.).

It was confirmed by observation with an electron microscope that this silicone microparticle was a microparticle whose silicone elastomer spherical microparticle surface was covered with a granular polymethylsilsesquioxane having diameter of 20 to 30 nm.

Dispersibility of this silicone microparticle was measured by the method described before; and the results shown in Table 1 were obtained.

Example 6

A silicone microparticle was obtained in a manner similar to that in Example 1 except that 6.6 g (this amount corresponds to 0.05 part by mass of tripolyoxyethylene stearyl ammonium chloride relative to 100 parts by mass of water) of 20% tripolyoxyethylene stearyl ammonium chloride (trade name of Catinal SPC-20AC; manufactured by Toho Chemical Industry Co., Ltd.) was used instead of 3.3 g of the 40% aqueous solution of dimethyl diallyl ammonium chloride polymer (trade name of ME Polymer H40W; manufactured by Toho Chemical Industry Co., Ltd.) in Example 1.

The silicone microparticles thus obtained were dispersed into water by using a surfactant; and particle size distribution similar to that of the aqueous disperse solution of the foregoing silicone elastomer microparticles, having volume-average particle diameter of 3 µm, was obtained by a particle size distribution measurement instrument using an electric resistance method (Multisizer 3; manufactured by Beckman Coulter, Inc.).

It was confirmed by observation with an electron microscope that this silicone microparticle was a microparticle whose silicone elastomer spherical microparticle surface was covered with a granular polymethylsilsesquioxane having diameter of 20 to 30 nm.

Dispersibility of this silicone microparticle was measured by the method described before; and the results shown in Table 1 were obtained.

Comparative Example 1

A silicone microparticle was obtained in a manner similar to that in Example 1 except that the 40% aqueous solution of dimethyl diallyl ammonium chloride polymer (trade name of ME Polymer H40W; manufactured by Toho Chemical Industry Co., Ltd.) in Example 1 was not used.

The silicone microparticles thus obtained were dispersed into water by using a surfactant; and particle size distribution similar to that of the aqueous disperse solution of the foregoing silicone elastomer microparticles, having volume-average particle diameter of 3 µm, was obtained by a particle size distribution measurement instrument using an electric resistance method (Multisizer 3; manufactured by Beckman Coulter, Inc.).

It was confirmed by observation with an electron microscope that this silicone microparticle was a microparticle whose silicone elastomer spherical microparticle surface was covered with a granular polymethylsilsesquioxane having diameter of 70 to 100 nm.

Dispersibility of this silicone microparticle was measured by the method described before; and the results shown in Table 1 were obtained.

Comparative Example 2

A silicone microparticle was obtained in a manner similar to that in Example 1 except that 1.3 g (this amount corresponds to 0.05 part by mass relative to 100 parts by mass of water) of sodium lauryl sulfate (trade name of Nikkol SLS; manufactured by Nikko Chemicals Co., Ltd.) was used instead of 3.3 g of the 40% aqueous solution of dimethyl diallyl ammonium chloride polymer (trade name of ME Polymer H40W; manufactured by Toho Chemical Industry Co., Ltd.) in Example 1; but this was not flowable.

The silicone microparticles thus obtained were dispersed into water by using a surfactant; and particle size distribution thereof was measured by a particle size distribution measurement instrument using an electric resistance method (Multisizer 3; manufactured by Beckman Coulter, Inc.). It was found in the particle size distribution that there were many particles having larger size than the silicone elastomer microparticles in the foregoing aqueous disperse solution, with the volume-average particle diameter thereof being 17 µm, suggesting that the particle thereof has a strong agglomeration tendency so that the particle may not be broken to primary particles in water.

This silicone microparticle was observed with an electron microscope; and it was found that amount of the polymethylsilsesquioxane granule adhered onto surface of the silicone elastomer spherical microparticle was small, with the size of the granule being 100 nm.

Dispersibility of this silicone microparticle was measured by the method described before; and the results shown in Table 1 were obtained.

TABLE 1

| | Cationic surfactant or Cationic water-soluble polymer | | Diameter of polymethyl- | Dispersibility (Sieve-passed amount: %) | | |
|---|---|---|---|---|---|---|
| Items | Chemical name | Amount g/100 g of $H_2O$ | silsesquioxane granule (nm) | 60 Mesh | 100 Mesh | 200 Mesh |
| Example 1 | Dimethyl dially ammonium chloride polymer | 0.05 | 10 to 20 | 98 | 92 | 85 |
| Example 2 | Cationic cellulose | 0.05 | 30 to 60 | 94 | 88 | 74 |

TABLE 1-continued

| Items | Cationic surfactant or Cationic water-soluble polymer Chemical name | Amount g/100 g of $H_2O$ | Diameter of polymethyl- silsesquioxane granule (nm) | Dispersibility (Sieve-passed amount: %) 60 Mesh | 100 Mesh | 200 Mesh |
|---|---|---|---|---|---|---|
| Example 3 | Dodecyl trimethyl ammonium chloride | 0.05 | 20 to 30 | 97 | 89 | 81 |
| Example 4 | Polyethylene imine | 0.05 | 30 to 40 | 94 | 87 | 77 |
| Example 5 | Dialkyl dimethyl ammonium chloride | 0.05 | 20 to 30 | 99 | 89 | 80 |
| Example 6 | Tripolyoxy-ethylene stearyl ammonium chloride | 0.05 | 20 to 30 | 97 | 90 | 81 |
| Comparative Example 1 | — | 0 | 70 to 100 | 91 | 84 | 57 |
| Comparative Example 2 | (Sodium lauryl sulfate - anionic surfactant- was added instead) | 0 | 100 (amount was small) | 7 | 1 | 0 |

Example 7

Into a 1-L glass beaker were taken 114 g of a methyl vinyl polysiloxane having a dynamic viscosity of 10 mm²/second as shown by the following formula (3) and 400 g of an organohydrogen polysiloxane having a dynamic viscosity of 110 mm²/second as shown by the following formula (4) (blending ratio of the hydrosilyl group to the olefinic unsaturated group is 1.04 to 1), and they were dissolved by agitation with a homomixer at 2000 rpm. Thereafter, 1 g of polyoxyethylene lauryl ether (addition number of moles of ethylene oxide is 9 mole) and 100 g of water were added thereinto; and then, the resulting mixture was agitated by using a homomixer at 6000 rpm, whereby giving an oil-in-water state having increased viscosity; the agitation was continued for further 15 minutes. Then, 382 g of water was added thereinto with agitation at 2000 rpm to obtain a white, homogenous emulsion. This emulsion was transferred to a 1-L glass flask equipped with an agitator having an anchor blade; and after the temperature thereof was adjusted at 15 to 20° C., a dissolved mixture solution comprising 1.6 g of a toluene solution of a chloroplatinic acid-olefin complex (Pt content of 0.5%) and 1 g of polyoxyethylene lauryl ether (addition number of moles of ethylene oxide is 9 mole) was added thereinto; and then, the resulting mixture was agitated for 12 hours at the same temperature to obtain an aqueous disperse solution of silicone elastomer microparticles.

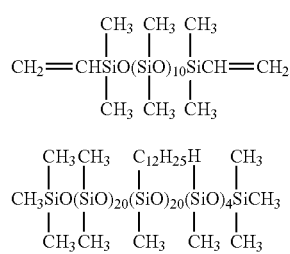

Shape of the silicone elastomer microparticle in the aqueous disperse solution thus obtained was spherical by observation with an optical microscope; and the volume-average particle diameter thereof measured by a particle size distribution measurement instrument using an electric resistance method (Multisizer 3; manufactured by Beckman Coulter, Inc.) was 12 μm.

Hardness of the silicone elastomer to constitute the silicone elastomer microparticle was measured as following. A methyl vinyl polysiloxane shown by the formula (3), an organohydrogen polysiloxane shown by the formula (4), and a toluene solution of a chloroplatinic acid-olefin complex (Pt content of 0.5%) were mixed with the foregoing mixing ratio; and then, the resulting mixture was poured into an aluminum petri dish so as to give the depth of 10 mm. It was allowed to stand at 25° C. for 24 hours, and then heated in a constant temperature oven controlled at 50° C. for one hour to obtain an unsticky silicone elastomer. Hardness of the silicone elastomer was 44 as measured with a durometer E hardness meter.

Into a 3-L glass flask equipped with an agitator having an anchor blade was transferred 876 g of the aqueous disperse solution containing the silicone elastomer spherical particles obtained as described above; and thereinto were added 1988 g of water, 57 g of a 28% aqueous ammonia solution, and 3.1 g (this amount corresponds to 0.05 part by mass of dimethyl diallyl ammonium chloride polymer relative to 100 parts by mass of water) of a 40% aqueous solution of dimethyl diallyl ammonium chloride polymer (trade name of ME Polymer H40W; manufactured by Toho Chemical Industry Co., Ltd.). At this point of time, pH of the solution was 11.3. After the temperature of the resulting mixture was adjusted at 5 to 10° C., 79 g of methyl trimethoxy silane (this amount corresponds to 8.6 parts by mass of the polymethylsilsesquioxane after the hydrolysis-condensation reaction relative to 100 parts by mass of the silicone elastomer spherical microparticle) was gradually added thereinto over 30 minutes; and then, agitation was further continued for one hour while maintaining the solution temperature at 5 to 10° C. Then, the temperature thereof was raised till 55 to 60° C.; and then, agitation was continued for one hour while maintaining the same temperature to complete the hydrolysis-condensation reaction of methyl trimethoxy silane.

The solution obtained after the hydrolysis-condensation reaction of methyl trimethoxy silane in the aqueous disperse solution of the silicone elastomer microparticles was dehydrated by using a filter press till water content therein of about 30%. The dehydrated matter was transferred to a 5-L glass flask equipped with an agitator having an anchor blade, and then, 3000 g of water was added thereinto; after agitation was continued for 30 minutes, dehydration was done by using a filter press. The dehydrated matter thus obtained was transferred again to the 5-L glass flask equipped with an agitator having an anchor blade, added with 3000 g of water, agitated for 30 minutes, and then dehydrated by using a filter press. The dehydrated matter was dried with a fluidized bed drier using a hot air of 105° C.; then, the dried matter thus obtained was crushed with a jet mill to obtain free-flowing silicone microparticles.

The silicone microparticles thus obtained were dispersed into water by using a surfactant; and particle size distribution similar to that of the aqueous disperse solution of the foregoing silicone elastomer microparticles, having volume-average particle diameter of 12 μm, was obtained by a particle size distribution measurement instrument using an electric resistance method (Multisizer 3; manufactured by Beckman Coulter, Inc.).

It was confirmed by observation with an electron microscope that this silicone microparticle was a microparticle whose silicone elastomer spherical microparticle surface was covered with a granular polymethylsilsesquioxane having diameter of 10 to 20 nm.

Dispersibility of this silicone microparticle was measured by the method described before; and the results shown in Table 2 were obtained.

Example 8

A silicone microparticle was obtained in a manner similar to that in Example 7 except that 1.2 g (this amount corresponds to 0.02 parts by mass of tripolyoxyethylene stearyl ammonium chloride relative to 100 parts by mass of water) of the 40% aqueous solution of dimethyl diallyl ammonium chloride polymer (trade name of ME Polymer H40W; manufactured by Toho Chemical Industry Co., Ltd.) in Example 7 was used instead of 3.1 g of that.

The silicone microparticles thus obtained were dispersed into water by using a surfactant; and particle size distribution similar to that of the aqueous disperse solution of the foregoing silicone elastomer microparticles, having volume-average particle diameter of 12 μm, was obtained by a particle size distribution measurement instrument using an electric resistance method (Multisizer 3; manufactured by Beckman Coulter, Inc.).

It was confirmed by observation with an electron microscope that this silicone microparticle was a microparticle whose silicone elastomer spherical microparticle surface was covered with a granular polymethylsilsesquioxane having diameter of 20 to 30 nm.

Dispersibility of this silicone microparticle was measured by the method described before; and the results shown in Table 2 were obtained.

Comparative Example 3

A silicone microparticle was obtained in a manner similar to that in Example 7 except that the 40% aqueous solution of dimethyl diallyl ammonium chloride polymer (trade name of ME Polymer H40W; manufactured by Toho Chemical Industry Co., Ltd.) in Example 7 was not used.

The silicone microparticles thus obtained were dispersed into water by using a surfactant; and particle size distribution thereof was measured by a particle size distribution measurement instrument using an electric resistance method (Multisizer 3; manufactured by Beckman Coulter, Inc.). It was found in the particle size distribution that there were many particles having larger size than the silicone elastomer microparticles in the foregoing aqueous disperse solution, with the volume-average particle diameter thereof being 35 μm, suggesting that the particle thereof has a strong agglomeration tendency so that the particle may not be broken to primary particles in water.

It was confirmed by observation with an electron microscope that this silicone microparticle was a microparticle whose silicone elastomer spherical microparticle surface was covered with a granular polymethylsilsesquioxane having diameter of 100 nm.

Dispersibility of this silicone microparticle was measured by the method described before; and the results shown in Table 2 were obtained.

TABLE 2

| Items | Cationic surfactant or Cationic water-soluble polymer | | Diameter of polymethyl-silsesquioxane granule (nm) | Dispersibility (Sieve-passed amount: %) | | |
|---|---|---|---|---|---|---|
| | Chemical name | Amount g/100 g of $H_2O$ | | 60 Mesh | 100 Mesh | 200 Mesh |
| Example 7 | Dimethyl dially ammonium chloride polymer | 0.05 | 10 to 20 | 96 | 89 | 36 |
| Example 8 | Dimethyl dially ammonium chloride polymer | 0.02 | 20 to 30 | 98 | 87 | 34 |
| Comparative Example 3 | — | 0 | 100 | 42 | 3 | 1 |

Example 9

Into a 3-L glass beaker were taken 273 g of a methyl vinyl polysiloxane having a dynamic viscosity of 67 mm²/second as shown by the following formula (5) and 42 g of an organohydrogen polysiloxane having a dynamic viscosity of 30 mm²/second as shown by the following formula (6) (blending ratio of the hydrosilyl group to the olefinic unsaturated group is 1.08 to 1), and they were dissolved by agitation with a homomixer at 2000 rpm. Thereafter, 1.8 g of polyoxyethylene behenyl ether (addition number of moles of ethylene oxide is 10 mole), 2.7 g of polyoxyethylene behenyl ether (addition number of ethylene oxide is 20 mole), and 72 g of water were added thereinto; and then, the resulting mixture was agitated by using a homomixer at 6000 rpm, whereby giving an oil-in-water state having increased viscosity; the agitation was continued for further 15 minutes. Then, after 2607 g of water was added thereinto with agitation at 2000 rpm, the resulting mixture was treated with a homogenizer with the pressure of 40 MPa twice to obtain a white, homogenous emulsion. This emulsion was transferred to a 3-L glass flask equipped with an agitator having an anchor blade; and after the temperature thereof was adjusted at 15 to 20° C., a dissolved mixture solution comprising 0.9 g of a toluene solution of a chloroplatinic acid-olefin complex (Pt content of 0.5%) and 0.9 g of polyoxyethylene behenyl ether (addition number of ethylene oxide is 10 mole) was added thereinto; and then, the resulting mixture was agitated for 12 hours at the same temperature to obtain an aqueous disperse solution of silicone elastomer microparticles.

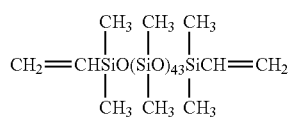

(5)

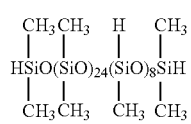

(6)

It was found by an optical microscope that shape of the silicone elastomer microparticle in the obtained aqueous disperse solution was spherical; and the volume-average particle diameter thereof was measured to be 0.7 μm with a particle size distribution measurement instrument of a laser diffraction/scattering type (LA-920; manufactured by HORIBA, Ltd.).

Hardness of the silicone elastomer to constitute the silicone elastomer microparticle was measured as following. A methyl vinyl polysiloxane shown by the formula (5), an organohydrogen polysiloxane shown by the formula (6), and a toluene solution of a chloroplatinic acid-olefin complex (Pt content of 0.5%) were mixed with the foregoing mixing ratio; and then, the resulting mixture was poured into an aluminum petri dish so as to give the depth of 10 mm. It was allowed to stand at 25° C. for 24 hours, and then heated in a constant temperature oven controlled at 50° C. for one hour to obtain an unsticky silicone elastomer. Hardness of the silicone elastomer was 51 as measured with a durometer A hardness meter.

Into a 3-L glass flask equipped with an agitator having an anchor blade was transferred 2871 g of the aqueous disperse solution containing the silicone elastomer spherical particles obtained as described above; and thereinto were added 60 g of a 28% aqueous ammonia solution, and 3.3 g (this amount corresponds to 0.05 part by mass of dimethyl diallyl ammonium chloride polymer relative to 100 parts by mass of water) of a 40% aqueous solution of dimethyl diallyl ammonium chloride polymer (trade name of ME Polymer H40W; manufactured by Toho Chemical Industry Co., Ltd.). At this point of time, pH of the solution was 11.4. After the temperature of the resulting mixture was adjusted at 5 to 10° C., 68 g of methyl trimethoxy silane (this amount corresponds to 11.1 parts by mass of the polymethylsilsesquioxane after the hydrolysis-condensation reaction relative to 100 parts by mass of the silicone elastomer spherical microparticle) was gradually added thereinto over 25 minutes; and then, agitation was further continued for one hour while maintaining the solution temperature at 5 to 10° C. Then, the temperature thereof was raised till 55 to 60° C.; and then, agitation was continued for one hour while maintaining the same temperature to complete the hydrolysis-condensation reaction of methyl trimethoxy silane.

The solution obtained after the hydrolysis-condensation reaction of methyl trimethoxy silane in the aqueous disperse solution of the silicone elastomer microparticles was dehydrated by using a filter press till water content therein of about 30%. The dehydrated matter was transferred to a 5-L glass flask equipped with an agitator having an anchor blade, and then, 3000 g of water was added thereinto; after agitation was continued for 30 minutes, dehydration was done by using a filter press. The dehydrated matter thus obtained was transferred again to the 5-L glass flask equipped with an agitator having an anchor blade, added with 3000 g of water, agitated for 30 minutes, and then dehydrated by using a filter press. The dehydrated matter was dried with a fluidized bed drier using a hot air of 105° C.; then, the dried matter thus obtained was crushed with a jet mill to obtain free-flowing silicone microparticles.

The silicone microparticles thus obtained were dispersed into water by using a surfactant; and particle size distribution similar to that of the aqueous disperse solution of the foregoing silicone elastomer microparticles, having volume-average particle diameter of 0.7 μm, was obtained by a particle size distribution measurement instrument of a laser diffraction/scattering type (LA-920; manufactured by HORIBA, Ltd.).

It was confirmed by observation with an electron microscope that this silicone microparticle was a microparticle whose silicone elastomer spherical microparticle surface was covered with a granular polymethylsilsesquioxane having diameter of 10 to 20 nm.

Dispersibility of this silicone microparticle was measured by the method described before; and the results shown in Table 3 were obtained.

Comparative Example 4

A silicone microparticle was obtained in a manner similar to that in Example 9 except that the 40% aqueous solution of dimethyl diallyl ammonium chloride polymer (trade name of ME Polymer H40W; manufactured by Toho Chemical Industry Co., Ltd.) in Example 9 was not used.

The silicone microparticles thus obtained were dispersed into water by using a surfactant; and particle size distribution thereof was measured by a particle size distribution measurement instrument of a laser diffraction/scattering type (LA-920; manufactured by HORIBA, Ltd.). It was found in the particle size distribution that there were many particles having larger size than the silicone elastomer microparticles in the foregoing aqueous disperse solution, with the volume-average particle diameter thereof being 1.2 μm, suggesting that the particle thereof has a strong agglomeration tendency so that the particle may not be broken to primary particles in water.

It was confirmed by observation with an electron microscope that this silicone microparticle was a microparticle whose silicone elastomer spherical microparticle surface was covered with a granular polymethylsilsesquioxane having diameter of 80 nm.

Dispersibility of this silicone microparticle was measured by the method described before; and the results shown in Table 3 were obtained.

TABLE 3

| Items | Cationic surfactant or Cationic water-soluble polymer | | Diameter of polymethyl- silsesquioxane granule (nm) | Dispersibility (Sieve-passed amount: %) | | |
|---|---|---|---|---|---|---|
| | Chemical name | Amount g/100 g of $H_2O$ | | 60 Mesh | 100 Mesh | 200 Mesh |
| Example 9 | Dimethyl dially ammonium chloride polymer | 0.05 | 10 to 20 | 71 | 63 | 39 |
| Comparative Example 4 | — | | 0 | 80 | 25 | 8 | 1 |

As shown in Tables 1 to 3, silicone microparticles of Examples 1 to 9 have higher dispersibility as compared with microparticles of Comparative Examples 1 to 4, especially even in the case of the silicone elastomer microparticles with low rubber hardness and small particle diameter, dispersibility thereof is far higher as compared with conventional particles; and thus, when this microparticle is blended in a resin or a cosmetic, homogeneous dispersion till primary particles without agglomeration may be obtained so that expression of desirable characteristics thereof may be expected. In addition, in a dry classification process, high classification performance may be expected.

It is to be noted that the present invention is not limited to the above embodiments. The above embodiments are merely illustrative, and whatever having the substantially same configurations as the technical concept recited in the appended claims and exhibiting the same functions and effects are embraced within the technical scope of the present invention.

What is claimed is:

1. A silicone microparticle, wherein the silicone microparticle comprises 100 parts by mass of a silicone elastomer spherical microparticle having volume-average particle diameter of 0.1 to 100 μm and 0.5 to 25 parts by mass of a polyorganosilsesquioxane to cover surface of the silicone elastomer spherical microparticle, wherein the polyorganosilsesquioxane has a shape of granule with the size thereof being 60 nm or less.

2. The silicone microparticle according to claim 1, wherein volume-average particle diameter of the silicone elastomer spherical microparticle is 0.1 to 5 μm.

3. The silicone microparticle according to claim 1, wherein rubber hardness of a silicone elastomer to constitute the silicone elastomer spherical microparticle is 10 or more as measured with a type E durometer and 30 or less as measured with a type A durometer.

4. The silicone microparticle according to claim 2, wherein rubber hardness of a silicone elastomer to constitute the silicone elastomer spherical microparticle is 10 or more as measured with a type E durometer and 30 or less as measured with a type A durometer.

5. A method for producing a silicone microparticle, wherein a hydrolysis-condensation of an organotrialkoxy silane is carried out in the presence of water, a silicone elastomer spherical microparticle having volume-average particle diameter of 0.1 to 100 μm, an basic substance, and a cationic surfactant and/or a cationic water-soluble polymer, whereby covering surface of the silicone elastomer spherical microparticle with a polyorganosilsesquioxane to produce the silicone microparticle according to claim 1.

6. A method for producing a silicone microparticle, wherein a hydrolysis-condensation of an organotrialkoxy silane is carried out in the presence of water, a silicone elastomer spherical microparticle having volume-average particle diameter of 0.1 to 100 μm, an basic substance, and a cationic surfactant and/or a cationic water-soluble polymer, whereby covering surface of the silicone elastomer spherical microparticle with a polyorganosilsesquioxane to produce the silicone microparticle according to claim 2.

7. A method for producing a silicone microparticle, wherein a hydrolysis-condensation of an organotrialkoxy silane is carried out in the presence of water, a silicone elastomer spherical microparticle having volume-average particle diameter of 0.1 to 100 μm, an basic substance, and a cationic surfactant and/or a cationic water-soluble polymer, whereby covering surface of the silicone elastomer spherical microparticle with a polyorganosilsesquioxane to produce the silicone microparticle according to claim 3.

8. A method for producing a silicone microparticle, wherein a hydrolysis-condensation of an organotrialkoxy silane is carried out in the presence of water, a silicone elastomer spherical microparticle having volume-average particle diameter of 0.1 to 100 μm, an basic substance, and a cationic surfactant and/or a cationic water-soluble polymer, whereby covering surface of the silicone elastomer spherical microparticle with a polyorganosilsesquioxane to produce the silicone microparticle according to claim 4.

9. The method for producing a silicone microparticle according to claim 5, wherein amount of the cationic surfactant and/or the cationic water-soluble polymer is 0.001 to 1 part by mass relative to 100 parts by mass of the water.

10. The method for producing a silicone microparticle according to claim 6, wherein amount of the cationic surfactant and/or the cationic water-soluble polymer is 0.001 to 1 part by mass relative to 100 parts by mass of the water.

11. The method for producing a silicone microparticle according to claim 7, wherein amount of the cationic surfactant and/or the cationic water-soluble polymer is 0.001 to 1 part by mass relative to 100 parts by mass of the water.

12. The method for producing a silicone microparticle according to claim 8, wherein amount of the cationic surfactant and/or the cationic water-soluble polymer is 0.001 to 1 part by mass relative to 100 parts by mass of the water.

* * * * *